United States Patent
Antelman et al.

(10) Patent No.: US 11,147,777 B1
(45) Date of Patent: Oct. 19, 2021

(54) METHODS AND FORMULATIONS FOR EFFICACIOUS PAIN RELIEF BY TRANSDERMAL DELIVERY OF CANNABIDIOL

(71) Applicant: CHARLOTTE'S WEB, INC., Boulder, CO (US)

(72) Inventors: Perry Antelman, Sharon, MA (US); Bharat Madhavan, Kingston, RI (US); Shalom Lampert, Maalot (IL)

(73) Assignee: Charlotte's Web, Inc., Boulder, CO (US)

( * ) Notice: Subject to any disclaimer, the term of this patent is extended or adjusted under 35 U.S.C. 154(b) by 0 days.

(21) Appl. No.: 17/189,484

(22) Filed: Mar. 2, 2021

Related U.S. Application Data

(63) Continuation-in-part of application No. 16/010,587, filed on Jun. 18, 2018, now abandoned.

(60) Provisional application No. 62/520,692, filed on Jun. 16, 2017.

(51) Int. Cl.
| | |
|---|---|
| *A61K 31/05* | (2006.01) |
| *A61K 31/352* | (2006.01) |
| *A61K 9/06* | (2006.01) |
| *A61K 9/00* | (2006.01) |
| *A61K 31/045* | (2006.01) |
| *A61K 36/185* | (2006.01) |
| *A61K 47/44* | (2017.01) |

(52) U.S. Cl.
CPC ............ *A61K 31/05* (2013.01); *A61K 9/0014* (2013.01); *A61K 31/045* (2013.01); *A61K 36/185* (2013.01); *A61K 47/44* (2013.01)

(58) Field of Classification Search
CPC ........ A61K 9/0014; A61K 9/06; A61K 31/05; A61K 31/352
See application file for complete search history.

(56) References Cited

U.S. PATENT DOCUMENTS

| | | |
|---|---|---|
| 5,540,934 A | 7/1996 | Touitou |
| 6,132,762 A | 10/2000 | Cristobal |
| 9,375,417 B2 | 6/2016 | Smith et al. |
| 2003/0104016 A1 | 6/2003 | Gendimenico |
| 2011/0052694 A1 | 3/2011 | Stinchcomb et al. |
| 2012/0202891 A1 | 8/2012 | Stinchcomb et al. |
| 2012/0264818 A1 | 10/2012 | Newland |
| 2014/0200200 A1 | 7/2014 | Piazza |
| 2014/0271940 A1 | 9/2014 | Wurzer |
| 2014/0302148 A1 | 10/2014 | Winnicki |

FOREIGN PATENT DOCUMENTS

| | | |
|---|---|---|
| WO | 2018/085794 A1 | 5/2018 |

OTHER PUBLICATIONS

Eichner et al., Biochimica et Biophysica Acta vol. 1859 pp. 745-755 (2017).

*Primary Examiner* — Theodore R. Howell
(74) *Attorney, Agent, or Firm* — Daniel Feigelson

(57) ABSTRACT

Methods and formulations for providing efficacious pain relief by transdermal delivery of cannabidiol (CBD), the formulations having a high weight ratio of CBD to (-)-trans-$\Delta^9$-tetrahydrocannabinol (THC).

20 Claims, 9 Drawing Sheets

| Agonists | | % max icilin response | $EC_{50}$ |
|---|---|---|---|
| Icilin |  | 100 ± 4.7% | 0.2 ± 0.1 µM |
| Frescolat ML |  | 64 ± 5.9% | 3.3 ± 1.5 µM |
| WS-3 |  | 86 ± 3.4% | 3.7 ± 1.7 µM |
| (−)menthol |  | 71 ± 2.3% | 4.1 ± 1.3 µM |
| Frescolat MGA |  | 69 ± 2.2% | 4.8 ± 1.1 µM |
| Cooling-agent 10 |  | 65 ± 8.7% | 6 ± 2.2 µM |

FIG. 2 CONT'D

| Compound | Structure | % | Value |
|---|---|---|---|
| (+)menthol | 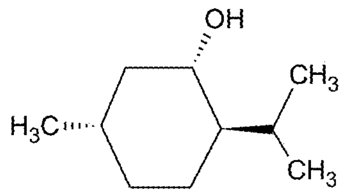 | 68 ± 4.1% | 14.4 ± 1.3 µM |
| PMD-38 | 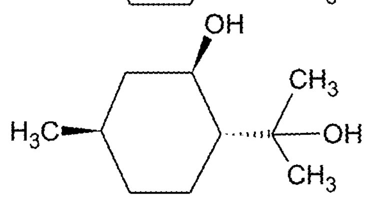 | 23 ± 2.2% | 31 ± 1.1 µM |
| WS-23 | 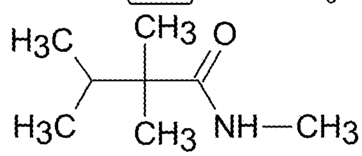 | 28 ± 4.4% | 44 ± 7.3 µM |
| Coolact P | 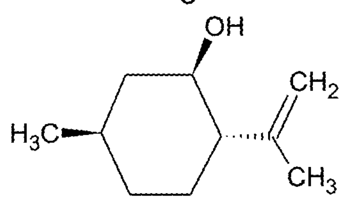 | 42 ± 6.2 % | 66 ± 1.2 µM |
| Geraniol | 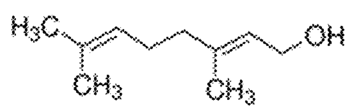 | 28 ± 1.1% | 5.9 ± 1.6 mM |
| Linalool | 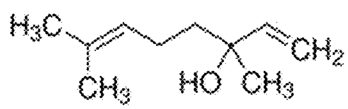 | 21 ± 1.1% | 6.7 ± 2.0 mM |
| Eucalyptol | 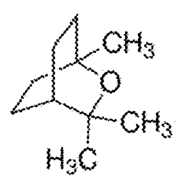 | 23 ± 2.4 % | 7.7 ± 2.0 mM |
| Hydroxy-citronellal | 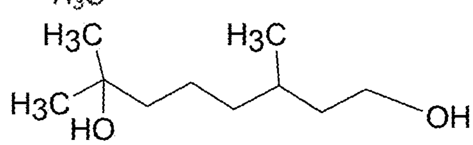 | 15 ± 0.7% | 19.6 ± 2.2 mM |
| Eugenol | 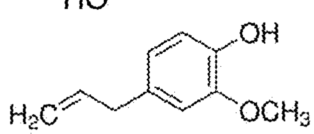 | Inactive | Inactive |
| Citral | 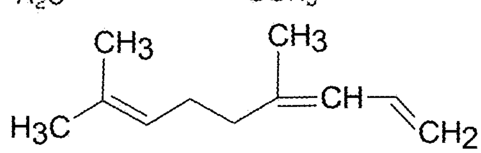 | Inactive | Inactive |

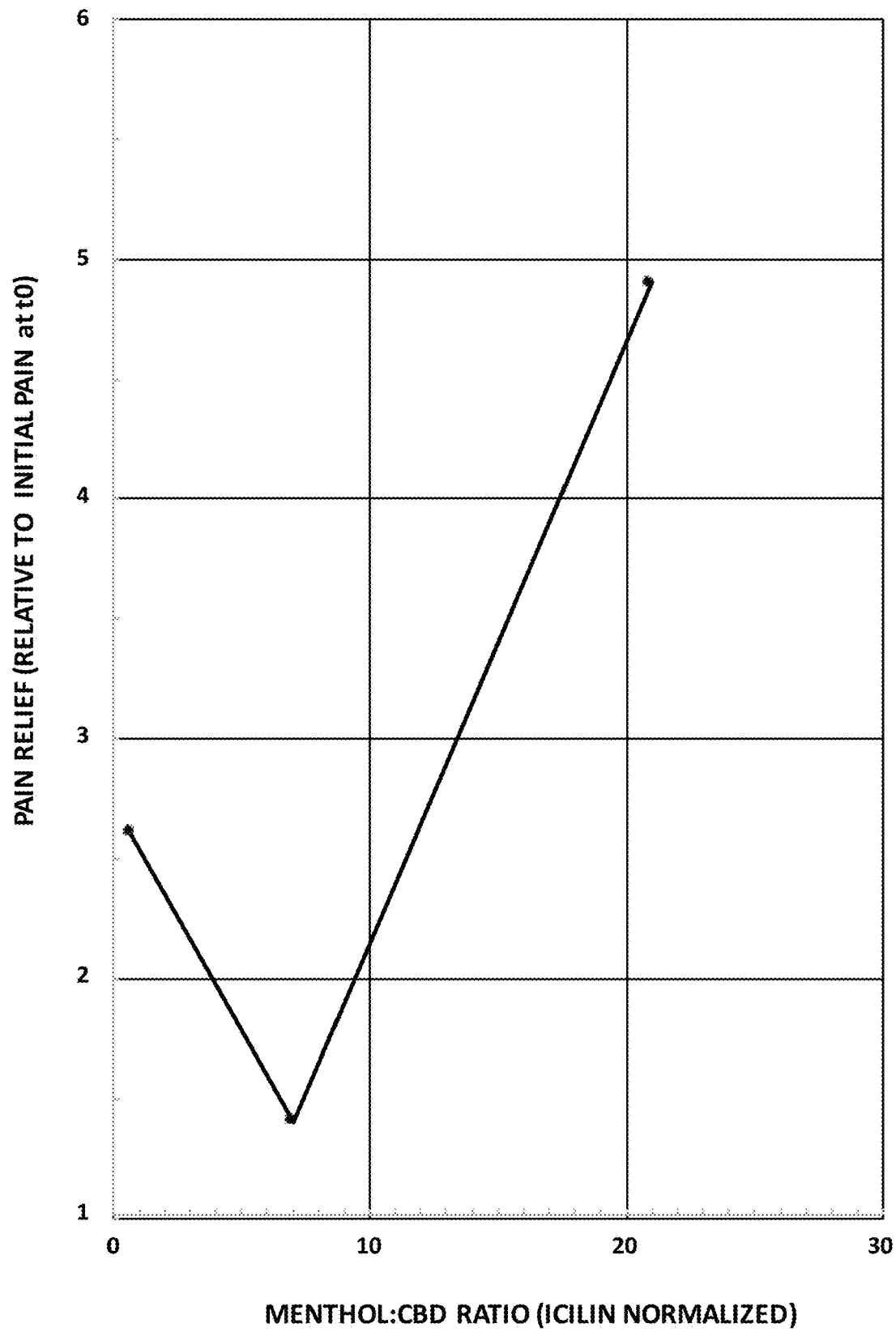

US 11,147,777 B1

METHODS AND FORMULATIONS FOR EFFICACIOUS PAIN RELIEF BY TRANSDERMAL DELIVERY OF CANNABIDIOL

RELATED APPLICATIONS

This application is a Continuation-in-Part of U.S. patent application Ser. No. 16/010,587, filed Jun. 18, 2018, which claims the benefit of U.S. Provisional Patent Application Ser. No. 62/520,692, filed Jun. 16, 2017, both of which are incorporated by reference for all purposes as if fully set forth herein.

FIELD AND BACKGROUND OF THE INVENTION

The present invention generally relates to the transdermal delivery of cannabidiol, and more particularly, to methods and formulations for effecting the transdermal delivery of cannabidiol.

Cannabidiol (CBD), a type of cannabinoid, is the major non-psychoactive component of *cannabis*. Various cannabinoids are known to exhibit relief of inflammatory pain. In contrast to oral delivery, transdermal delivery of cannabinoids enables specific areas of the body (e.g., of a muscle or joint) to be targeted for treatment. More specifically, CBD may be used, at different concentrations to target various cell membrane receptors, nuclear receptors, intra-cellular uptake transporters, and cannabinoid binding proteins. Perhaps the best known of the targeted receptors are the CB1 and CB2 receptors.

While significant advances have been made over recent years, the present inventors have recognized a need for improved methods and formulations for the transdermal delivery of CBD.

SUMMARY OF THE INVENTION

According to aspects of the present invention there is provided a topical formulation for application to the skin, the topical formulation including a cannabidiol (CBD), and a carrier material therefor. Most typically, the formulations have a high weight ratio of CBD to $(-)$-trans-$\Delta^9$-tetrahydrocannabinol (THC).

The topical formulations may be particularly efficacious in the topical treatment of various medical conditions, including muscle, joint, and connective tissue pain, arthritis, rheumatoid arthritis, and peripheral neuropathic pain.

In some aspects of the present invention, the formulations include at least one, and typically at least two, or at least three, agonists of a transient receptor potential melastatin cation channel member 8 (TRPM8).

In some embodiments of the present invention, the formulations include a total concentration of TRPM8 agonists of at least 2.5%, on an icilin-normalized scale.

In some embodiments of the present invention, the formulations have a high weight ratio of at least 7:1, and typically higher, between the total, icilin-normalized concentration of TRPM8 agonists and the CBD.

According to aspects of the present invention there is provided a topical formulation for application to the skin, the topical formulation including: (a) a cannabidiol (CBD), at a concentration of at least 0.10%, by weight; (b) at least one agonist of a transient receptor potential melastatin cation channel member 8 (TRPM8), wherein a total concentration of the at least one TRPM8 agonist on an icilin-normalized scale is at least 2.5%; and (c) a carrier for the CBD and the at least one TRPM8 agonist; wherein the topical formulation has a first weight ratio ($R_{C/T}$) defined by the concentration of the CBD to a concentration of $(-)$-trans-$\Delta^9$-tetrahydrocannabinol (THC), wherein the first weight ratio ($R_{C/T}$) is at least 5:1; wherein the topical formulation has a second weight ratio ($R_{A/C}$) defined by the total concentration of the at least one TRPM8 agonist, to the CBD concentration, and wherein the second weight ratio ($R_{A/C}$) is at least 7:1.

According to aspects of the present invention there is provided a topical formulation for application to the skin, the topical formulation including: (a) a cannabidiol (CBD), at a concentration of at least 0.15%, by weight; (b) menthol, at a concentration ($C_{Men}$) of at least 7%, by weight; (c) optionally camphor, having a concentration ($C_{Cam}$); and (d) a carrier for the CBD, the menthol, and the camphor; wherein the topical formulation has a first weight ratio ($R_{C/T}$) defined by the concentration of the CBD to a concentration of $(-)$-trans-$\Delta^9$-tetrahydrocannabinol (THC), wherein the first weight ratio ($R_{C/T}$) is at least 5:1; wherein the topical formulation has an additional weight ratio defined by a total concentration of the menthol and the camphor ($C_{Men}+C_{Cam}$), to the CBD concentration, and wherein the additional weight ratio is at least 20:1.

In some embodiments of the present invention, the concentration of the CBD is at least 0.12%, at least 0.15%, at least 0.20%, at least 0.25%, at least 0.30%, at least 0.35%, at least 0.40%, or at least 0.45%.

In some embodiments of the present invention, the concentration of the CBD is at most 3%, at most 2.5%, at most 2%, at most 1.5%, at most 1.2%, at most 1%, at most 0.9%, at most 0.8%, at most 0.7%, at most 0.65%, or at most 0.6%.

In some embodiments of the present invention, the concentration of the CBD is within a range of 0.10 to 3%, 0.10 to 1.5%, 0.10 to 0.8%, 0.12 to 3%, 0.12 to 1.5%, 0.12 to 0.8%, 0.15 to 3%, 0.15 to 1.5%, 0.15 to 0.8%, 0.20 to 3%, 0.20 to 1.5%, 0.25 to 0.8%, 0.25 to 3%, 0.12 to 1.5%, 0.25 to 0.8%, 0.3 to 3%, 0.3 to 1.5%, 0.3 to 0.8%, 0.35 to 3%, 0.35 to 1.5%, 0.35 to 0.8%, 0.3 to 0.65%, 0.36 to 3%, 0.36 to 1.5%, 0.36 to 0.8%, 0.36 to 0.65%, 0.42 to 3%, 0.42 to 1.5%, 0.42 to 0.8%, 0.42 to 0.65%, or 0.42 to 0.6%.

In some embodiments of the present invention, the first weight ratio $R_{C/T}$ is at most 80:1, at most 70:1, at most 60:1, or at most 50:1.

In some embodiments of the present invention, the first weight ratio $R_{C/T}$ is at least 10:1, at least 20:1, at least 25:1, at least 30:1, at least 35:1, or at least 40:1.

In some embodiments of the present invention, the first weight ratio $R_{C/T}$ is within a range of 5:1 to 95:1, 20:1 to 95:1, 20:1 to 90:1, 5:1 to 95:1, 30:1 to 95:1, 30:1 to 90:1, 30:1 to 85:1, 30:1 to 80:1, 35:1 to 95:1, 35:1 to 90:1, 35:1 to 85:1, 35:1 to 80:1, 35:1 to 70:1, 40:1 to 95:1, 40:1 to 85:1, 40:1 to 80:1, or 40:1 to 70:1.

In some embodiments of the present invention, the second weight ratio ($R_{A/C}$) is at least 8:1, at least 10:1, at least 12:1, at least 14:1, at least 17:1, or at least 20:1.

In some embodiments of the present invention, the second weight ratio ($R_{A/C}$) is within a range of 7:1 to 100:1, 7:1 to 80:1, 7:1 to 60:1, 10:1 to 100:1, 10:1 to 80:1, 10:1 to 60:1, 15:1 to 100:1, 15:1 to 80:1, 15:1 to 60:1, 18:1 to 100:1, 22:1 to 80:1, 18:1 to 60:1, 22:1 to 100:1, 22:1 to 80:1, or 22:1 to 60:1.

In some embodiments of the present invention, the topical formulation further includes camphor.

In some embodiments of the present invention, the camphor concentration within the topical formulation is at least 1%, at least 2%, at least 3%, at least 4%, at least 5%, at least 7%, at least 9%, or at least 10%.

In some embodiments of the present invention, the camphor concentration within the topical formulation is at most 25%, at most 20%, at most 18%, at most 16%, at most 14%, at most 12%, or at most 11%.

In some embodiments of the present invention, the camphor concentration within the topical formulation is within a range of 1% to 25%, 2% to 20%, 3% to 20%, 4% to 20%, 4% to 18%, 4% to 16%, 4% to 14%, 4% to 12%, 6% to 20%, 6% to 18%, 6% to 16%, 6% to 14%, 6% to 12%, 8% to 20%, 8% to 18%, 8% to 16%, 8% to 14%, 8% to 12%, 10% to 20%, 10% to 18%, 10% to 16%, 10% to 14%, or 10% to 12%.

In some embodiments of the present invention, the at least one TRPM8 agonist includes menthol.

In some embodiments of the present invention, the total concentration of the at least one TRPM8 agonist includes at least 4%, at least 6%, at least 8%, at least 10%, at least 12%, or at least 14% menthol.

In some embodiments of the present invention, the concentration of menthol within the topical formulation is at most 32%, at most 25%, at most 20%, at most 18%, at most 16%, at most 14%, or at most 12%.

In some embodiments of the present invention, the concentration of menthol within the topical formulation is within a range of 1% to 32%, 2% to 25%, 3% to 25%, 4% to 25%, 4% to 20%, 4% to 18%, 4% to 16%, 6% to 25%, 6% to 20%, 6% to 18%, 6% to 16%, 8% to 25%, 8% to 20%, 8% to 18%, 8% to 16%, 10% to 25%, 10% to 20%, 10% to 18%, 10% to 16%, 12% to 25%, 12% to 20%, 12% to 18%, or 12% to 16%.

In some embodiments of the present invention, the total concentration of the at least one TRPM8 agonist, on the icilin-normalized scale, and camphor, within the topical formulation, is within a range of 4% to 35%, 4% to 30%, 4% to 25%, 5% to 35%, 5% to 30%, 5% to 25%, 6% to 35%, 6% to 30%, 6% to 25%, 8% to 35%, 8% to 30%, 8% to 25%, 8% to 23%, 10% to 35%, 10% to 30%, 10% to 25%, 10% to 23%, 15% to 35%, 15% to 30%, 15% to 25%, 18% to 35%, 18% to 30%, 18% to 25%, 18% to 23%, 20% to 35%, 20% to 30%, 20% to 27%, or 20% to 25%.

In some embodiments of the present invention, the topical formulation contains at most 20%, at most 15%, at most 10%, at most 5%, at most 2%, at most 1%, or substantially 0% water, by weight.

In some embodiments of the present invention, the concentration of lipophilic materials within the topical formulation is at least 90%, at least 95%, at least 97%, at least 98%, at least 99%, or substantially 100%.

In some embodiments of the present invention, the concentration of wax or beeswax within the topical formulation is at least 5%, at least 10%, at least 12%, at least 15%, or at least 18%, by weight, and optionally, within a range of 5 to 35%, 5 to 30%, 5 to 28%, 10 to 35%, 10 to 30%, 10 to 28%, 15 to 35%, 15 to 30%, 15 to 28%, 18 to 35%, 18 to 30%, or 18 to 28%.

In some embodiments of the present invention, the topical formulation further includes up to 0.2% of at least one of silver(I) oxide, $Ag_4O_4$, silver(I) carboxylate, and silver(II) carboxylate.

In some embodiments of the present invention, the topical formulation further includes at least one of zinc oxide or magnesium oxide.

In some embodiments of the present invention, the CBD includes, consists mainly (at least 50% by weight) of, or consists essentially or substantially of a CBD containing native, connatural or unacquired terpenes.

In some embodiments of the present invention, the weight percentage based ratio of a concentration of the native, connatural, co-derived, or unacquired terpenes to the concentration of the CBD is at least 20%, at least 35%, at least 50%, at least 75%, at least 100%, or at least 150%, and optionally, less than 400%, less than 300%, or less than 200%, and further optionally, within a range of 20 to 200%.

In some embodiments of the present invention, the topical formulation has an additional weight ratio defined by a total concentration of the menthol and the camphor ($C_{Men}+C_{Cam}$), to the CBD concentration, wherein the additional weight ratio is at least 20:1, at least 25:1, at least 30:1, at least 40:1, or at least 50:1.

In some embodiments of the present invention, the topical formulation is a pharmaceutical formulation.

In some embodiments of the present invention, the topical formulation is in a form of an ointment, a cream, an emulsion, or a lotion.

In some embodiments of the present invention, the topical formulation further includes any of the features provided herein.

According to aspects of the present invention there is provided a topical formulation such as a massage oil formulation, for application to the skin, the topical formulation including: (a) a cannabidiol (CBD), at a concentration of at least 0.01%, by weight; (b) a receptor-targeting agent including at least one of: (i) at least one agonist of a transient receptor potential melastatin cation channel member 8 (TRPM8), wherein a total concentration of the at least one TRPM8 agonist on an icilin-normalized scale is at least 2.5%; and (ii) camphor; wherein a total concentration of the at least one TRPM8 agonist and the camphor is at least 1.2%; and (c) a carrier liquid containing at least one biocompatible oil; the CBD and the receptor-targeting agent dissolved in the carrier liquid; wherein the topical formulation has a first weight ratio ($R_{C/T}$) of the CBD to a (–)-trans-$\Delta^9$-tetrahydrocannabinol (THC) of least 5:1; wherein the topical oil formulation fulfills at least one of the following: (i) a concentration of lipophilic materials within the topical oil formulation is at least 97%, at least 98%, at least 99%, or substantially 100%; (ii) a concentration of water within the topical oil formulation is at most 5%, at most 3%, at most 2%, at most 1%, at most 0.5% or is substantially 0%; (iii) a total concentration of the at least one biocompatible oil within the topical oil formulation is at least 60%, at least 65%, at least 70%, at least 75%, at least 80%, at least 85%, or at least 90%; and (iv) a total concentration of the at least one biocompatible oil, the at least one TRPM8 agonist and the camphor, within the topical oil formulation, is at least 80%, at least 85%, at least 90%, at least 95%, or at least 97%; and (v) a second weight ratio of a total concentration of the receptor-targeting agent to the CBD concentration, within the topical oil formulation is least 20:1, at least 40:1, at least 60:1, at least 80:1 at least 100:1, or at least 200:1, and optionally, at most 600:1, at most 500:1, or at most 400:1.

In some embodiments of the present invention, the concentration of CBD is at least 0.02%, at least 0.4%, at least 0.06%, at least 0.08%, at least 0.10%, at least 0.12%, at least 0.15%, at least 0.20%, at least 0.25%, at least 0.30%, at least 0.35%, at least 0.40%, or at least 0.45%, and optionally, at most 0.8%, at most 0.6%, at most 0.5%.

In some embodiments of the present invention, the concentration of CBD is within a range of 0.01% to 0.5%, 0.01% to 0.35%, 0.01% to 0.20%, 0.01% to 0.15%, 0.01% to 0.10%, 0.01% to 0.05%, 0.02% to 0.10%, 0.02% to 0.07%, 0.02% to 0.05%, 0.03% to 0.10%, or 0.03% to 0.05%.

In some embodiments of the present invention, the topical formulation further includes any of the features provided in the present Description.

According to aspects of the present invention there is provided a method of transdermally applying a topical formulation to a skin tissue, the method including: (a) providing the topical formulation as described hereinabove or in the Description hereinbelow; and (b) applying the topical formulation to the skin tissue.

In some embodiments of the present invention, the method further includes rubbing the topical formulation into the skin tissue.

According to aspects of the present invention there is provided a method of transdermally applying a topical formulation to a skin tissue, the method including: (a) applying, to the skin tissue, a topical formulation as described hereinabove or in the Description hereinbelow; and (b) rubbing the topical formulation into the skin tissue.

According to aspects of the present invention there is provided a method of transdermally applying a topical formulation to a skin tissue, the method including: (a) providing the topical formulation as described hereinabove or in the Description hereinbelow; and (b) applying the topical formulation, to the skin tissue, in a therapeutically effective amount to treat a medical condition, wherein the medical condition is selected from the group consisting of: muscle pain, joint pain, arthritis, rheumatoid arthritis, and peripheral neuropathic pain.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention.

In the drawings:

FIG. 3D plots the pain relief achieved for several formulations, 8 hours after the time of application ($t_0$), as a function of the icilin-normalized menthol:CBD ratio;

DESCRIPTION OF THE PREFERRED EMBODIMENTS

Figure 1:
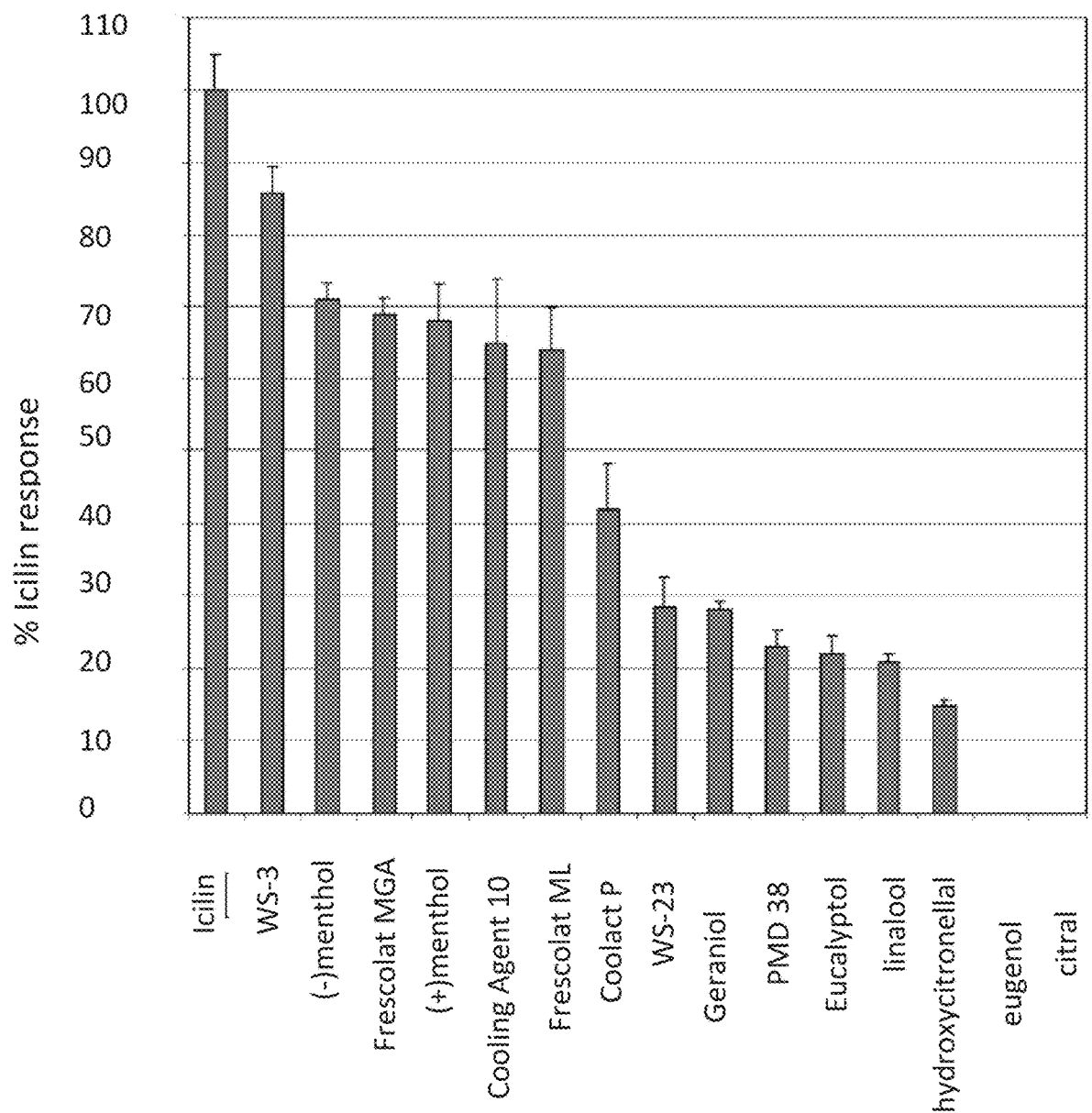
FIG. 1 is a bar graph showing the relative efficacy of various TRPM8 agonists, normalized to the maximum icilin response.

The principles of the formulations and treatment methods of the present invention may be better understood with reference to the drawings and the accompanying description. It is to be understood that the phraseology and terminology employed herein is for the purpose of description and should not be regarded as limiting.

The CBD-rich plant (*cannabis*, hemp, etc.) extract or concentrate (e.g., hemp extract) may be prepared by any of various methods known in the art, including solvent extraction using organic solvents (e.g., heptane, isopropyl alcohol, ethanol), or supercritical $CO_2$. The separation of the solvent from the extract may similarly be effected by known methods. The CBD-rich extract is typically produced as an oil. It may be particularly advantageous to use a raw material that has a naturally high ratio of CBD to THC. Various strains have been bred for this purpose, and extracts therefrom are commercially-available. Such extracts contain various terpenes and terpenoid substances that may lend additional efficacy to the transdermally delivered formulations of the present invention. Without wishing to be limited, these substances may include α-pinene, β-pinene, limonene, camphene, sabinene, Δ-3-carene, α-phellandrene, β-myrcene, α-terpinene, various cineoles, γ-terpinene, cis-β-ocimene, trans-β-ocimene, α-terpinolene, and β-caryophyllene.

The CBD-rich hemp extract used in the Examples provided below is characterized by a high content of CBD (~10%) and a high ratio of CBD to THC (over 40 to 1). This extract was supplied by Charlotte's Web (Colorado, USA). Advantageously, this CBD-rich hemp extract contains a large portion of the native, connatural terpenes and terpenoid substances that originate in the hemp plant raw material.

In some embodiments of the present invention, the formulations have a high weight ratio of at least 7:1, and typically higher, between the total, icilin-normalized concentration of TRPM8 agonists and the CBD. Without wishing to be limited by theory, the inventors believe that the CBD may or antagonize the TRPM8 site or channel. Surprisingly, by utilizing a suitably large quantity of TRPM8 agonists, the channel may be effectively blocked, thereby providing additional therapeutic efficacy to the formulation and treatment methods of the present invention.

In addition, and again, without wishing to be limited by theory, the inventors believe that menthol (both d- and l-forms), as well as various other TRPM8 agonists, may behave differently with respect to the TRPM8 channel, depending on the available concentration of the agonist at the site. While at lower concentrations, menthol and some other TRPM8 agonists may activate the receptor, at higher concentrations, these agonists may actually reverse their function, thereby serving to block the TRPM8 channel.

This blocking of the receptor may serve to desensitize, contributing to the user's feeling of pain alleviation and well-being.

EXAMPLES

Reference is now made to the following examples, which together with the above descriptions, illustrate the invention in a non-limiting fashion.

Example 1

Formulation of Creams, Lotions, and Water-Based Emulsions

1. Purified and distilled water was heated to about 50° C. in a vessel;
2. With the aid of a homogenizer, appropriate amounts of sorbic acid (or other natural preservatives), active materials (e.g., TRPM8 agonist materials and camphor) and powders (ZnO, MgO, AgO) were dispersed in the aqueous phase;
3. In a separate vessel, the oil phase was prepared by introducing appropriate amounts of lipophilic ingredients (CBD-rich concentrate or plant extract shea butter, emulsifying wax, vegetable oils, jojoba oil, and the like), and melting and mixing them by means of a hot plate, typically to 60-65° C.;
4. Once the oil phase is sufficiently melted and mixed, the oil phase is transferred to the aqueous phase, under vigorous/high shear mixing, by means of the homogenizer;
5. Homogenizing is effected until the desired consistency is attained.

Example 2

Formulation of an Oil-Based Product

1. Carrier oil (e.g., olive oil, cottonseed oil, vegetable oil, jojoba oil, as well as combinations thereof) was heated in a vessel, on a hot plate, to about 65° C.;
2. The TRPM8 agonist materials and optional camphor were added to the oil and allowed to dissolve. A homogenizer was used to facilitate dispersion;
3. Appropriate amounts of beeswax pellets, petrolatum, etc., were added and allowed to dissolve with the aid of the homogenizer;
4. The heat was controlled to gradually reduce the temperature;
5. At about 60° C., various essential oils and other optional ingredients (e.g., AgO, ZnO, MgO) were introduced with the CBD concentrate (typically a CBD-rich, THC-poor whole plant extract);
6. Gradual cooling down was effected to produce the CBD-containing ointment or oil-based product.

Example 3

Formulation of Massage Oils

1. Carrier oil (cottonseed oil, vegetable oil, jojoba oil, olive oil, etc., as well as combinations thereof) was heated up to 140° F./60° C. in a stirred vessel;
2. Active materials (e.g., menthol, camphor) were added with CBD rich whole plant extract and dissolved with the aid of the mixer, until the massage oil components are fully dissolved and homogenized.

Example 4

A water-based formulation was prepared according to the method of Example 1. The composition was as follows:

| | |
|---|---|
| Purified Water | 67.00% |
| Jojoba Oil | 6.40% |
| Bentonite Clay | 6.00% |
| Silver Oxide | 0.10% |
| Magnesium Oxide | 2.00% |
| Zinc Oxide | 4.00% |
| Sorbic Acid | 0.50% |
| Hemp Extract (CBD10 %) | 10.00% |
| Lidocaine HCl | 4.00% |

Example 5

A water-based formulation was prepared according to the method of Example 1. The composition was as follows:

| | |
|---|---|
| Purified Water | 60.90% |
| Jojoba Oil | 16.00% |
| Bentonite Clay | 2.50% |
| Silver Oxide | 0.10% |
| Magnesium Oxide | 4.00% |
| Zinc Oxide | 2.00% |
| Sorbic Acid | 0.50% |
| Hemp Extract (CBD10 %) | 10.00% |
| Menthol | 4.00% |

Example 6

A water-based formulation was prepared according to the method of Example 1. The composition was as follows:

| | |
|---|---|
| Purified Water | 40.40% |
| Olive Oil | 5.00% |
| Xanthum Gum | 2.00% |
| Emulsifying Wax | 14.00% |
| Silver Oxide | 0.10% |
| Magnesium Oxide | 1.00% |
| Zinc Oxide | 1.00% |
| Sorbic Acid | 0.50% |
| Hemp Extract (CBD10 %) | 20.00% |
| Camphor | 8.00% |
| Menthol | 8.00% |

Example 7

A water-based formulation was prepared according to the method of Example 1. The composition was as follows:

| | |
|---|---|
| Purified Water | 83.49% |
| Gelling Agent (Genopol) | 5.00% |
| Silver Oxide | 0.01% |
| Magnesium Oxide | 1.00% |
| Zinc Oxide | 1.00% |
| Sorbic Acid | 0.50% |
| Hemp Extract (CBD10 %) | 5.00% |
| Menthol | 4.00% |

Example 8

A water-based formulation was prepared according to the method of Example 1. The composition was as follows:

| | |
|---|---|
| Purified Water | 60.00% |
| Argan Oil | 1.00% |
| Shea Butter | 5.00% |
| Emulsifying Wax | 7.50% |
| Magnesium Oxide | 2.00% |
| Zinc Oxide | 2.00% |
| Sorbic Acid | 0.50% |
| Hemp Extract (CBD10 %) | 5.00% |
| Camphor | 3.00% |
| Menthol | 14.00% |

Example 9

A water-based formulation was prepared according to the method of Example 1. The composition was as follows:

| | |
|---|---|
| Purified Water | 44.00% |
| Jojoba Oil | 1.00% |
| Cottonseed Oil | 2.00% |
| Silver Carbwrylate | 0.01% |
| Shea Butter | 12.00% |
| Emulsifying Wax | 13.00% |
| Magnesium Oxide | 0.05% |
| Zinc Oxide | 0.05% |
| Sorbic Acid | 0.80% |
| Peppermint Oil | 0.50% |
| Tea Tree Oil | 0.50% |
| Eucalyptus Oil | 1.00% |
| Clove Oil | 2.00% |
| Hemp Extract | 2.34% |
| Menthol | 10.30% |
| Camphor | 10.50% |

Example 10

A water-based formulation was prepared according to the method of Example 1. The composition was as follows:

| | |
|---|---|
| Purified Water | 61.30% |
| Jojoba Oil | 1.00% |
| Cottonseed Oil | 2.00% |
| Silver Wax | 0.01% |
| Shea Butter | 12.00% |
| Emulsifying Wax | 13.00% |
| Magnesium Oxide | 0.05% |
| Zinc Oxide | 0.05% |
| Sorbic Acid | 0.80% |
| Peppermint Oil | 0.50% |
| Tea Tree Oil | 0.50% |
| Eucalyptus Oil | 1.00% |
| Clove Oil | 2.00% |
| Hemp Extract | 1.67% |
| Menthol | 4.12% |

Example 11

An oil-based formulation was prepared according to the method of Example 2. The composition was as follows:

| | |
|---|---|
| Cottonseed Oil | 56.20% |
| Beeswax | 24.00% |
| Jojoba Oil | 1.00% |
| Silver Wax | 0.05% |
| Eucalyptus Oil | 1.00% |
| Clove Oil | 2.00% |
| Hemp Extract | 2.23% |
| Zinc Oxide | 0.05% |
| Magnesium Oxide | 0.05% |
| Peppermint Oil | 0.50% |
| Tea Tree Oil | 0.50% |
| Menthol | 7.2% |
| Camphor | 5.3% |

Example 12

An oil-based formulation was prepared according to the method of Example 2. The composition was as follows:

| | |
|---|---|
| Jojoba Oil | 53.90% |
| Beeswax | 24.48% |
| Silver Oxide | 0.02% |
| Palmarosa Oil | 2.00% |
| Sage Oil | 2.00% |
| Zinc Oxide | 0.05% |
| Magnesium Oxide | 0.05% |
| Hemp Extract (CBD10 %) | 2.50% |
| Camphor | 5.00% |
| Menthol | 10.00% |

Example 13

An oil-based formulation was prepared according to the method of Example 2. The composition was as follows:

| | |
|---|---|
| Soybean Oil | 14.00% |
| Cotton Seed Oil | 17.39% |
| Petrolatum | 30.00% |
| Beeswax | 25.00% |
| Silver Oxide | 0.01% |
| Palmarosa Oil | 2.00% |
| Sage Oil | 2.00% |
| Zinc Oxide | 0.05% |
| Magnesium Oxide | 0.05% |
| Hemp Extract (CBD10 %) | 2.50% |
| Camphor | 3.00% |
| Menthol | 4.00% |

Example 14

An oil-based formulation was prepared according to the method of Example 2. The composition was as follows:

| | |
|---|---|
| Mineral Oil | 21.50% |
| Petrolatum | 18.49% |
| Synthetic wax (AC629) | 21.00% |
| Beeswax | 1.00% |
| Silver Oxide | 0.01% |
| Tea Tree Oil | 2.00% |
| Eucalyptus Oil | 2.00% |
| Zinc Oxide | 1.00% |
| Magnesium Oxide | 1.00% |
| Hemp Extract (CBD10 %) | 5.00% |
| Camphor | 11.00% |
| Menthol | 16.00% |

Example 15

An oil-based formulation was prepared according to the method of Example 2. The composition was as follows:

| | |
|---|---|
| Cottonseed Oil | 42.41% |
| Beeswax | 21.60% |
| Jojoba Oil | 1.00% |
| Silver Wax | 0.01% |
| Eucalyptus Oil | 1.00% |
| Clove Oil | 2.00% |
| Hemp Extract | 4.63% |
| Sorbic Acid | 0.30% |
| Peppermint Oil | 0.50% |
| Tea Tree Oil | 0.50% |
| Zinc Oxide | 0.05% |
| Magnesium Oxide | 0.05% |
| Menthol | 15.45% |
| Camphor | 10.50% |

Example 16

An oil-based formulation was prepared according to the method of Example 2. The composition was as follows:

| | |
|---|---|
| Mineral Oil | 28.50% |
| Petrolatum | 35.00% |
| Stearic Acid | 11.30% |
| Silver Oxide | 0.20% |
| Tea Tree Oil | 1.00% |
| Eucalyptus Oil | 1.00% |
| Zinc Oxide | 1.00% |
| Magnesium Oxide | 1.00% |
| Hemp Extract (CBD10 %) | 5.00% |
| Camphor | 8.00% |
| Menthol | 8.00% |

Example 17

An oil-based formulation was prepared according to the method of Example 2. The composition was as follows:

| | |
|---|---|
| Mineral Oil | 9.50% |
| Petrolatum | 5.00% |
| Hydrogenated Soybean Oil | 33.00% |
| Beeswax | 5.30% |
| Silver Oxide | 0.20% |
| Tea Tree Oil | 1.00% |
| Peppermint Oil | 1.00% |
| Zinc Oxide | 2.00% |
| Magnesium Oxide | 2.00% |
| Hemp Extract (CBD10 %) | 25.00% |
| Camphor | 8.00% |
| Menthol | 8.00% |

Example 18

An oil-based formulation was prepared according to the method of Example 2. The composition was as follows:

| | |
|---|---|
| Cottonseed Oil | 47.5% |
| Beeswax | 24.0% |
| Jojoba Oil | 1.00% |
| Silver Carbwrylate | 0.03% |
| Eucalyptus Oil | 1.00% |
| Clove Oil | 2.00% |
| Hemp Extract | 2.32% |
| Sorbic Acid | 0.30% |
| Peppermint Oil | 0.50% |
| Tea Tree Oil | 0.50% |
| Zinc Oxide | 0.05% |
| Magnesium Oxide | 0.05% |
| Menthol | 10.30% |
| Camphor | 10.50% |

Example 19

An oil-based formulation was prepared according to the method of Example 2. The composition was as follows:

| | |
|---|---|
| Soybean Oil | 60.00% |
| Cottonseed Oil | 30.90% |
| Jojoba Oil | 2.60% |
| Argan Oil | 1.00% |
| Eucalyptus Oil | 2.00% |
| Hemp Extract | 0.50% |
| Camphor | 3.00% |

Example 20

A massage oil formulation was prepared according to the method of Example 3. The composition was as follows:

| | |
|---|---|
| Corn Oil | 55.00% |
| Olive Oil | 30.00% |
| Jojoba Oil | 3.00% |
| Eucalyptus Oil | 2.00% |
| Clove Oil | 1.00% |
| Hemp Extract | 1.00% |
| Camphor | 3.00% |
| Menthol | 5.00% |

Example 21

A massage oil formulation was prepared according to the method of Example 3. The composition was as follows:

| | |
|---|---|
| Soybean Oil | 45.00% |
| Olive Oil | 30.00% |
| Argan Oil | 3.00% |
| Tea Tree Oil | 3.00% |
| Clove Oil | 1.00% |
| Hemp Extract | 2.00% |
| Menthol | 16.00% |

Example 22

A massage oil formulation was prepared according to the method of Example 3. The composition was as follows:

| | |
|---|---|
| Jojoba Oil | 56.6% |
| Cottonseed Oil | 23.0% |
| Hemp Extract | 0.4% |
| Menthol | 15.0% |
| Camphor | 5.0% |

Example 23

A massage oil formulation was prepared according to the method of Example 3. The composition was as follows:

| | |
|---|---|
| Jojoba Oil | 62.7% |
| Cottonseed Oil | 25.0% |
| Peppermint Oil | 4.0% |
| Hemp Extract | 0.3% |
| Menthol | 8.0% |

Example 24

A massage oil formulation was prepared according to the method of Example 3. The composition was as follows:

| | |
|---|---|
| Jojoba Oil | 60.85% |
| Cottonseed Oil | 30.00% |
| Tea Tree Oil | 3.00% |
| Eucalyptus Oil | 2.00% |
| Clove Oil | 1.00% |
| Hemp Extract | 0.15% |
| Menthol | 3.00% |

Example 25

Formulation 1

An oil-based formulation was prepared according to the method of Example 2. The composition was as follows:

| | |
|---|---|
| Cottonseed Oil | 70.25% |
| Beeswax | 24.00% |
| Hemp Extract | 5.25% |
| Menthol | 0.50% |

The hemp extract contained about 9.5% CBD, the remainder being cottonseed oil. The weight ratio of menthol to CBD within the oil-based formulation is approximately 1:1, which is equivalent to about 0.7:1, on an icilin-normalized basis.

Example 26

Formulation 2

An oil-based formulation was prepared according to the method of Example 2. The ingredients were identical to those used in Example 25. The composition was as follows:

| | |
|---|---|
| Cottonseed Oil | 65.75% |
| Beeswax | 24.00% |
| Hemp Extract | 5.25% |
| Menthol | 5.00% |

The weight ratio of menthol to CBD within the oil-based formulation is approximately 10:1, which is equivalent to about 7:1, on an icilin-normalized basis.

Example 27

Formulation 3

An oil-based formulation was prepared according to the method of Example 2. The ingredients were identical to those used in Example 25. The composition was as follows:

| | |
|---|---|
| Cottonseed Oil | 54.75% |
| Beeswax | 25.00% |
| Hemp Extract | 5.25% |
| Menthol | 15.00% |

The weight ratio of menthol to CBD within the oil-based formulation is approximately 30:1, which is equivalent to about 21:1, on an icilin-normalized basis.

Example 28

Pain Relief Study

A comparative clinical study was performed to evaluate the pain-relief efficacy of various topical formulations was performed.

Procedure

In the initial visit (T0), inclusion and non-inclusion criteria were confirmed and a Visual Analog Scale (VAS) Pain Scale assessment was carried out by an expert grader. The product application was performed by the subject under technician supervision after T0 assessments. Each subject only applied one of the three investigational products, following previous randomization. After 30 minutes, 2 hours, 4 hours and 8 hours from product application, a VAS Pain Scale assessment was carried out by an expert grader and subjects answered to self-assessment questionnaires. During the visit, subjects remained at rest in a room for at least 15 minutes before the assessments.

Female and male subjects, aged between 47 and 65 years old (mean age: 56 years old), with chronic or acute musculoskeletal pain (shoulder, knee, elbow, low back pain, etc.) that typically treat pain with nonsteroidal anti-inflammatory drugs pain medication or topical creams, and having baseline VAS pain scale of greater than 2 on the back, neck or joints (elbow, knee or hips). Twenty-two study subjects were included in the study and all of them completed the study. The total length of the study per subject was 32 hours, including 24 washout hours.

The topical formulations used in the comparative study, Formulations 1-3, are described hereinabove in Examples 25-27, respectively.

Example 29

The results of the comparative clinical pain relief study of Example 28 are provided in the Table below:

| | menthol conc. (wt %) | CBD conc. (wt %) | RATIOS | | Pain Relief (VAS Scale) | | | |
|---|---|---|---|---|---|---|---|---|
| | | | wt to wt | icilin normalized | 30 min. | 2 hours | 4 hours | 8 hours |
| Form. #1 | 0.5 | 0.5 | 1:1 | 0.7:1 | 2.1 | 2.3 | 2.2 | 2.6 |
| Form. #2 | 5 | 0.5 | 10:1 | 7:1 | 1.8 | 2 | 2.3 | 1.4 |
| Form. #3 | 15 | 0.5 | 30:1 | 21:1 | 4.7 | 5.7 | 5.7 | 4.9 |

Figure 3A:
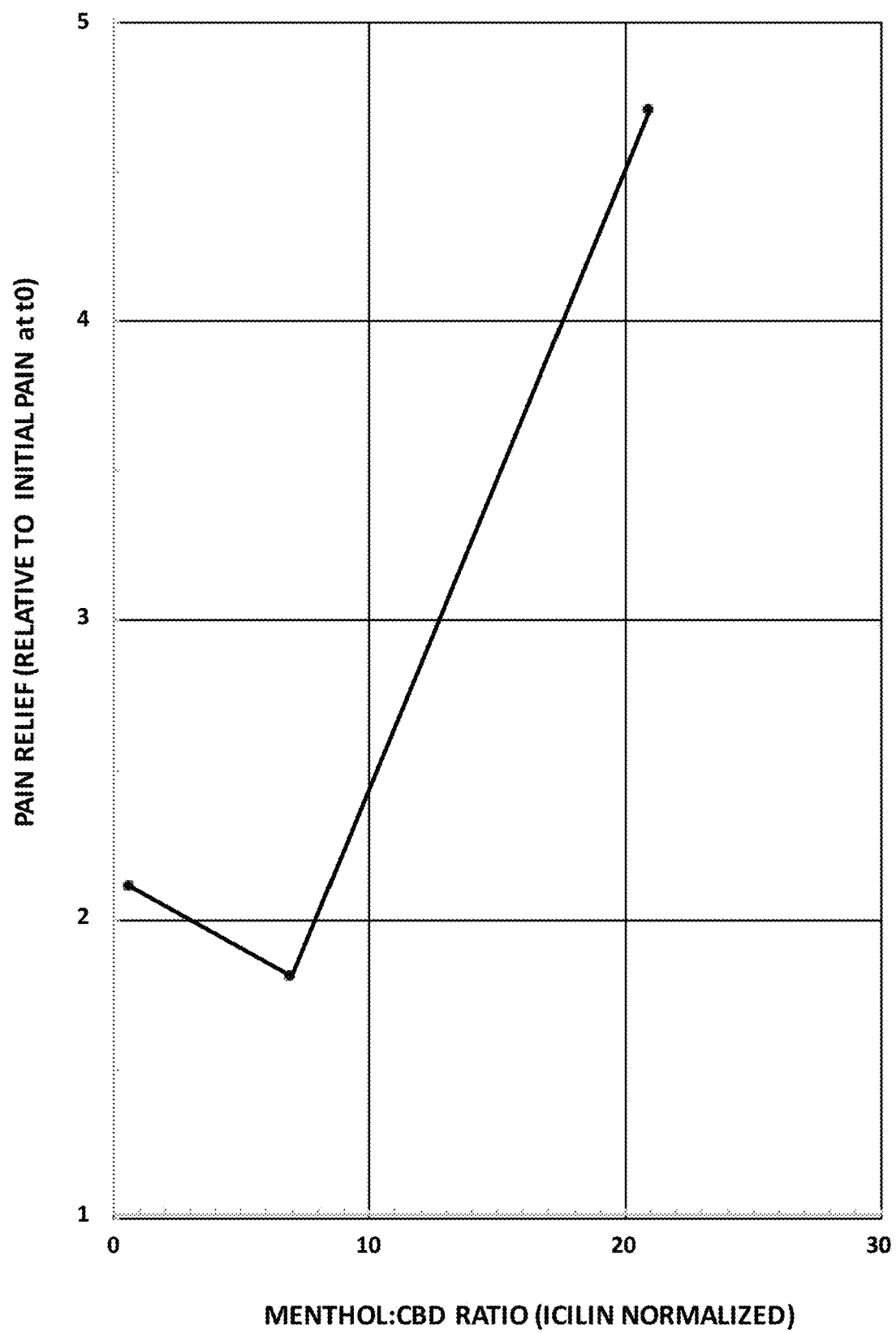
FIG. 3A plots the pain relief achieved for several formulations, 30 minutes after the time of application ($t_0$), as a function of the icilin-normalized menthol:CBD ratio.

FIG. 3A plots the pain relief achieved for each of the three formulations, 30 minutes after the time of application (to), as a function of the icilin-normalized menthol:CBD ratio (100 menthol=70 icilin). The pain relief is calculated by subtracting the initial VAS scale pain at to. It may be seen that the pain relief afforded by Formulation #3, at an icilin-normalized menthol:CBD ratio of 21:1, is more than double the pain relief afforded by Formulations #1 and #2.

Figure 3B:
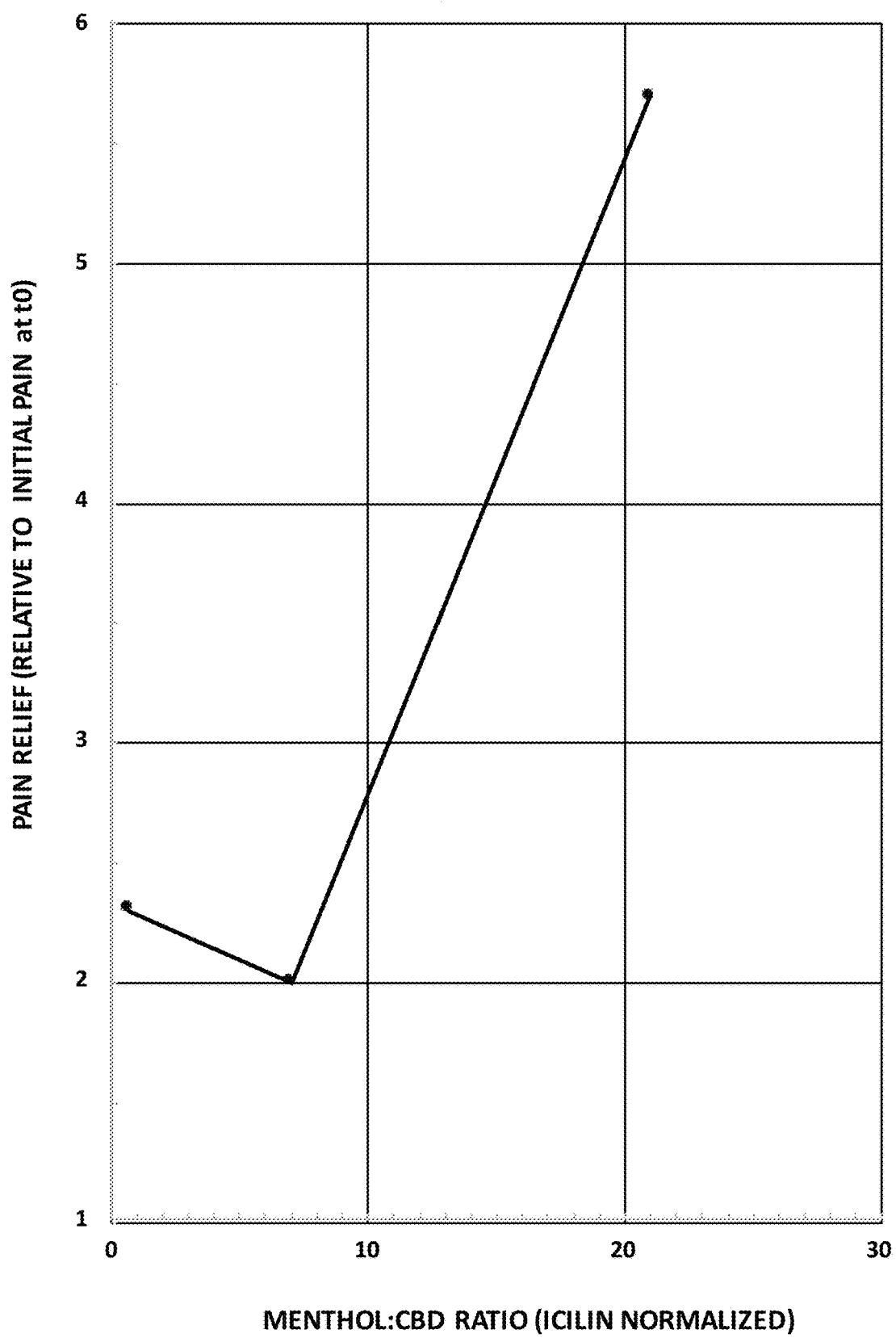
FIG. 3B plots the pain relief achieved for several formulations, 2 hours after the time of application ($t_0$), as a function of the icilin-normalized menthol:CBD ratio.
Figure 3C:
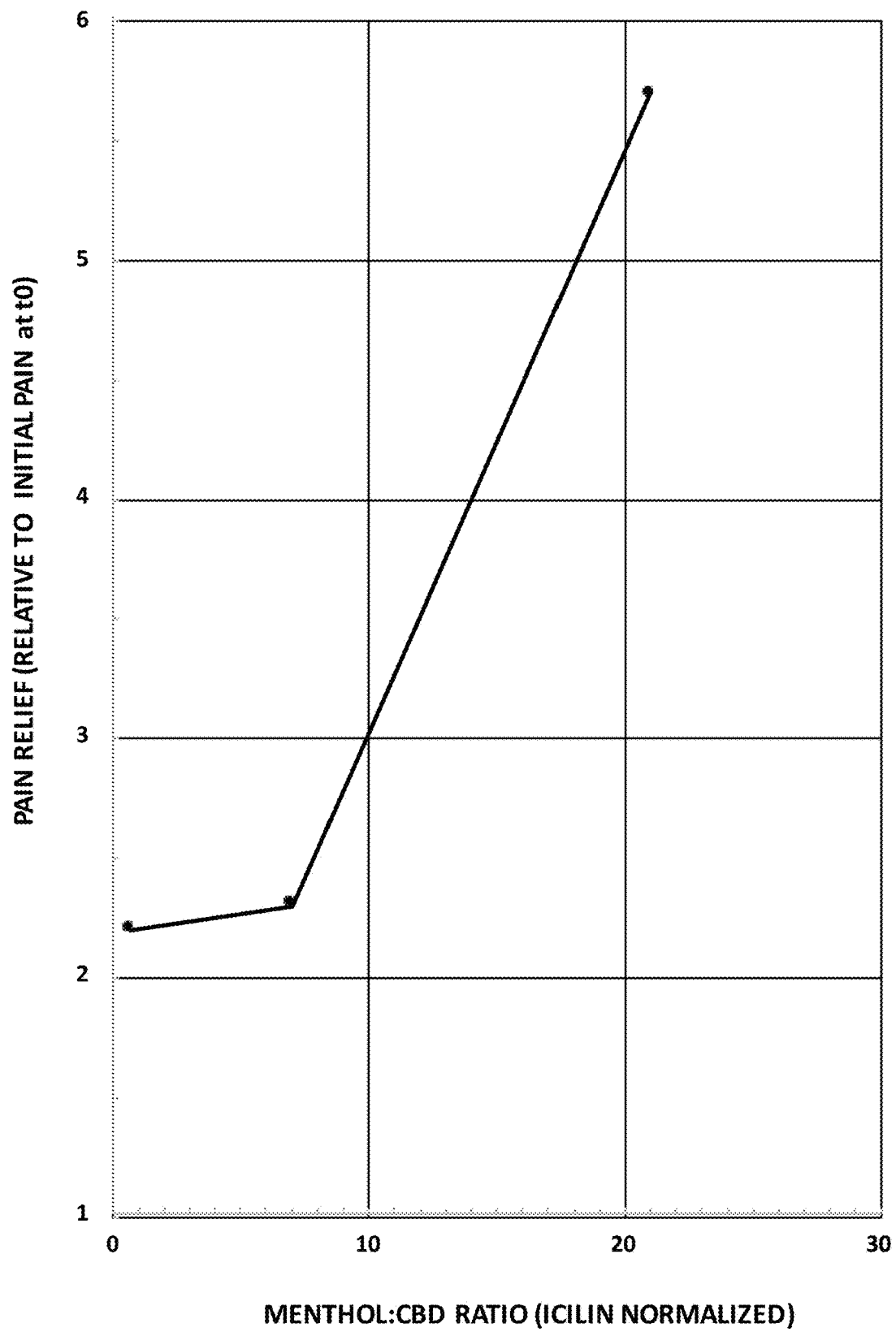
FIG. 3C plots the pain relief achieved for several formulations, 4 hours after the time of application ($t_0$), as a function of the icilin-normalized menthol:CBD ratio.

Similarly, FIGS. 3B-3D plot the pain relief achieved for each of the three formulations, at 2 hours, 4 hours, and 8 hours, respectively after to. Again, it may be seen that the pain relief afforded by Formulation #3, at an icilin-normalized menthol:CBD ratio of 21:1, is about double the pain relief afforded by Formulations #1 and #2.

Figure 4A:
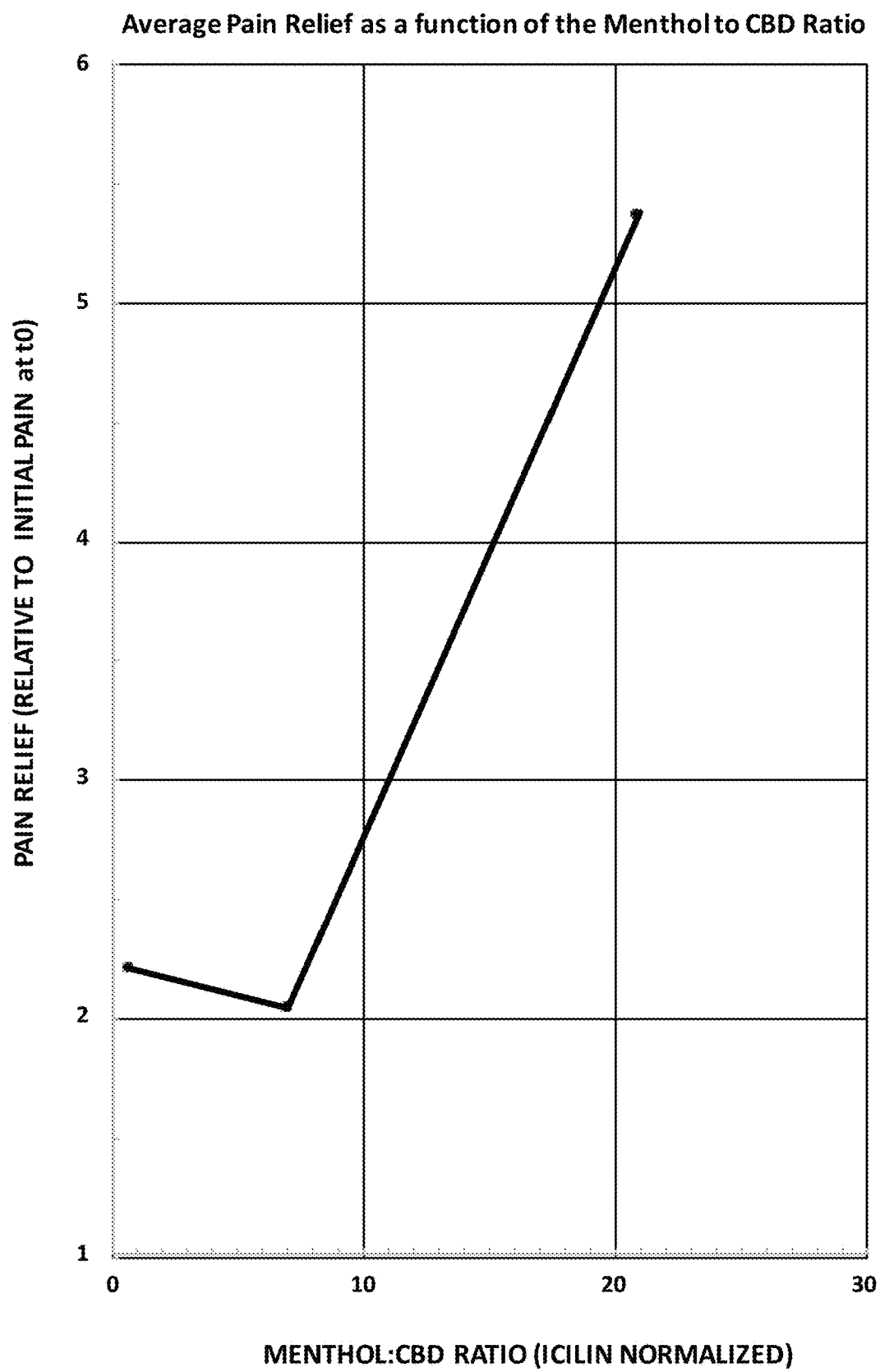
FIG. 4A plots the average pain relief achieved for each of these formulations, the average including the pain relief results for 30 minutes, 2 hours, and 4 hours after the time of application ($t_0$)

FIG. 4A plots the average pain relief achieved for each of the three formulations, after summing together the pain relief results for 30 minutes, 2 hours, and 4 hours after the time of application (to). It may be seen that on average, the pain relief afforded by Formulation #3, at an icilin-normalized menthol:CBD ratio of 21:1, exceeds the pain relief afforded by Formulations #1 and #2 by a factor of about 2.5. This is of particular significance because the temporary relief afforded by topical pain-relief formulations is often characterized within a time scale of up to 4 hours.

Figure 4B:
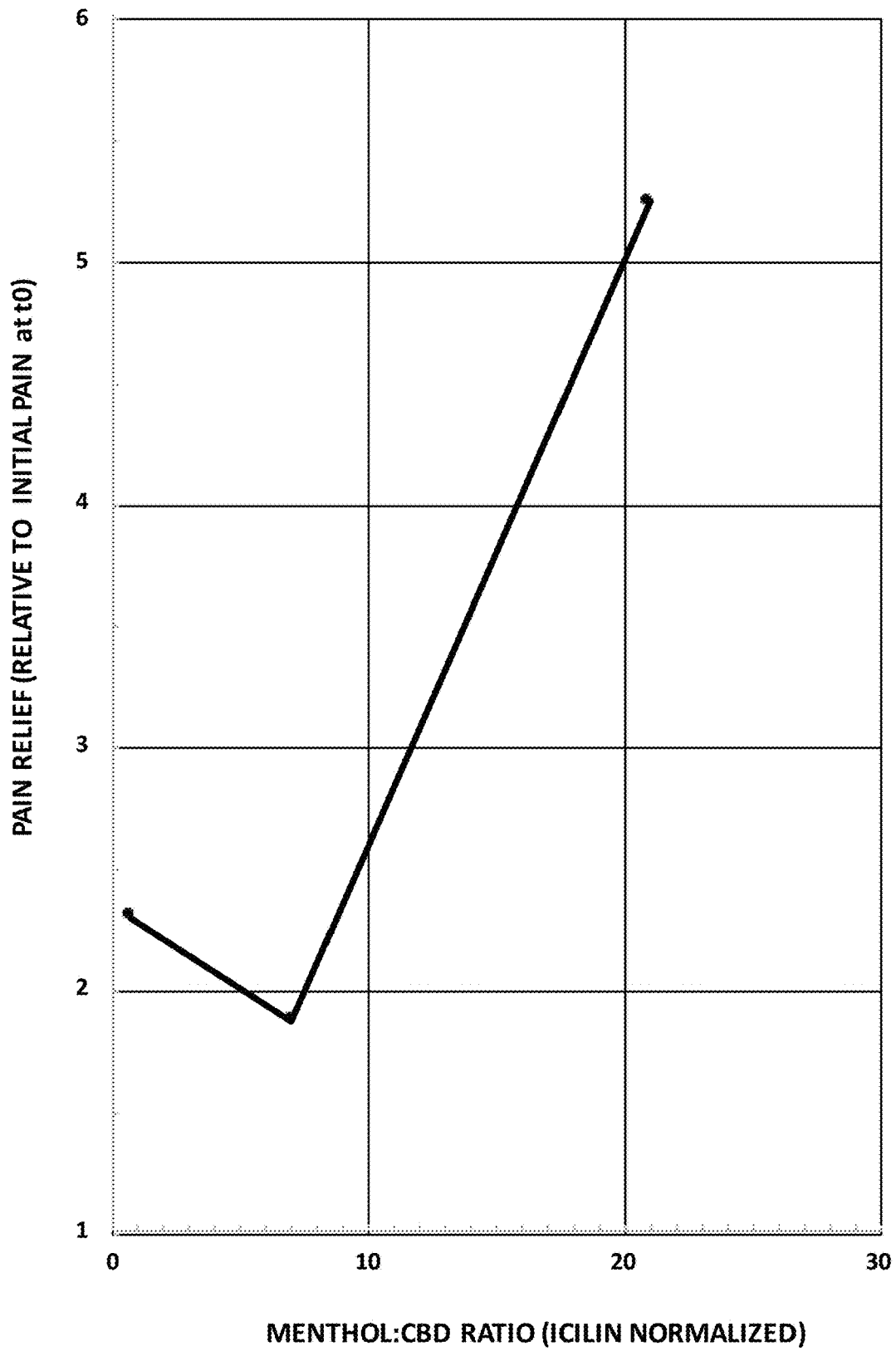
FIG. 4B plots the average pain relief achieved for each of these formulations, the average including the pain relief results for 30 minutes, 2 hours, 4 hours, and 8 hours after the time of application ($t_0$).

FIG. 4B plots the average pain relief achieved for each of the three formulations, after summing together the pain relief results for 30 minutes, 2 hours, 4 hours, and 8 hours after the time of application (to). Again, it may be seen that on average, the pain relief afforded by Formulation #3, at an icilin-normalized menthol:CBD ratio of 21:1, exceeds the pain relief afforded by Formulations #1 and #2 by a factor of about 2.5.

Measurement of $[Ca^{+2}]_i$ Using the FLIPR® Assay, and Data Analysis Thereof

In order to evaluate the efficacy of TRPM8 agonists, the following procedure, available in the literature (Behrendt et al., Characterization of the mouse cold-menthol receptor TRPM8 and vanilloid receptor type-1 VR1 using a fluorometric imaging plate reader (FLIPR) assay, British Journal of Pharmacology (2004) 141, 737-745), may be used. Those skilled in the art will be cognizant of minor changes that may be made in the procedure to accommodate other equipment, materials, etc.

mTRPM8- and hVR1-transfected HEK293 cells were seeded into black-walled clear-base poly-D-lysine-coated 96-well plates (Becton Dickinson, Meylan Cedex, France) at a density of 25,000 cells per well, as monolayers in minimum essential medium (MEM) supplemented with non-essential amino acids, 10% fetal calf serum and 0.2 mM L-glutamine, and maintained under 95% $O_2$/5% $CO_2$ at 37° C., and were cultured overnight. The cells were then incubated with MEM containing the cytoplasmic calcium indicator Fluo-4AM (4 µM; Molecular Probes, Eugene, Oreg., USA) at 37° C. for 30 minutes. The cells were washed twice with HBSS supplemented with 2.5 mM probenecid and 20 mM HEPES, resuspended in the same buffer, and incubated for 15 minutes at 37° C. Subsequently, the plates were inserted into a fluorometric imaging plate reader (FLIPR®; Molecular Devices, Sunnyvale, Calif., USA), and the fluorescence ($\lambda$ex=488 nM, $\lambda$em=510-570 nM) from $[Ca^{+2}]_i$ was determined before and after the addition of various concentrations of test compounds (SULLIVAN, E., TUCKER, E. M. & DALE, I. L. (1999), Measurement of $[Ca^{+2}]_i$ using the fluorometric imaging plate reader (FLIPR), Methods Mol. Biol., 114, 125-133; JERMAN, J. C., BROUGH, S. J., PRINJHA, R., HARRIES, M. H., DAVIS, J. B. & SMART, D. (2000), Characterization using FLIPR of rat vanilloid receptor (rVR1) pharmacology, Br. J. Pharmacol., 130, 916-922). Transfected cells were incubated at pH 6.3 for at least 1 minute prior to measurements.

With regard to data analysis, EC 50 values were determined as the concentration of test substance required to produce half-maximal increases in $[Ca^{+2}]_i$. Maximal $[Ca^{+2}]_i$ responses were measured as peak fluorescence intensity (FI) minus basal FI, and expressed as percentages of the maximum response to icilin. Data are given as means±s.e.m., unless otherwise stated. Curve fitting and parameter estimations were performed with Microsoft Excel 97 and Graph Pad Prism 3.01 (GraphPad Software Inc., CA, USA).

Referring now to the drawings, FIG. 1 is a bar graph showing the relative efficacy of various substances evaluated by Behrendt et al. for efficacy as TRPM8 agonists. The $[Ca^{+2}]_i$ responses were measured as maximal increases in fluorescence, expressed as percentages of the maximum icilin response, and are given as means±s.e.m. (n=4-8).

Figure 2:
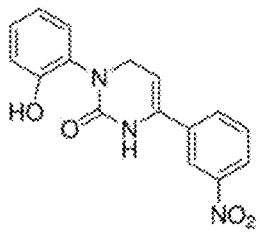
FIG. 2 provides, for the TRPM8 agonists of FIG. 1, the molecular structures and numerical data, as disclosed by Behrendt et al.
Figure 2:
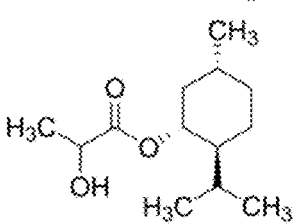
Figure 2:
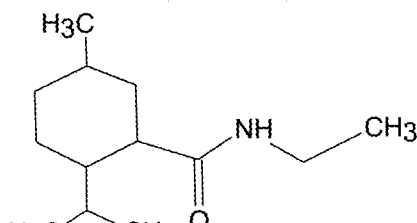
Figure 2:
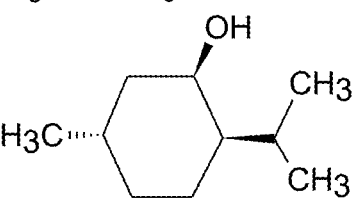
Figure 2:
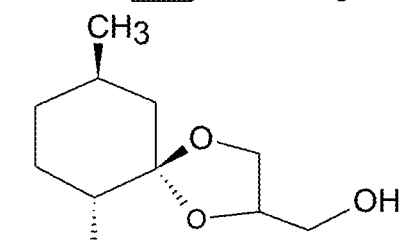
Figure 2:
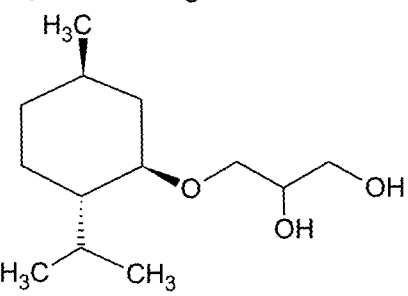

The molecular structures of the various substances, as well as numerical data, were also disclosed by Behrendt et al., and are provided in FIG. 2.

As used herein in the specification and in the claims section that follows, the term "TRPM8 agonist" and the like, is used as is conventionally used in the art.

As used herein in the specification and in the claims section that follows, the term "icilin-normalized scale" refers to a relative efficacy scale of TRPM8 agonists, normalized to the efficacy of icilin, as disclosed by Behrendt et al.

As used herein in the specification and in the claims section that follows, the term "skin", "application to the skin", etc., are meant to refer to mammalian skin, and most typically, human skin.

As used herein in the specification and in the claims section that follows, the term "percent", or "%", refers to percent by weight, unless specifically indicated otherwise.

Similarly, the term "ratio", as used herein in the specification and in the claims section that follows, refers to a weight ratio (weight per weight of the total formulation), unless specifically indicated otherwise.

The modifier "about" used in connection with a quantity is inclusive of the stated value and has the meaning dictated by the context (for example, it includes at least the degree of error associated with the measurement of the particular quantity). When used with a specific value, it should also be considered as disclosing that value.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification, including, but not limited to, US20140248379, are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A topical formulation for application to the skin, the topical formulation comprising:
    (a) cannabidiol (CBD), at a concentration of at least 0.10% by weight;
    (b) at least one agonist of a transient receptor potential melastatin cation channel member 8 (TRPM8), wherein the total concentration of said at least one TRPM8 agonist on an icilin-normalized scale is at least 2.5% by weight; said at least one TRPM8 agonist including menthol;
    (c) optionally, (−)-trans-$\Delta^9$-tetrahydrocannabinol (THC);
    (d) a carrier for said CBD, said at least one TRPM8 agonist, and, if present, said THC;
wherein, when said THC is present, the topical formulation has a first weight ratio ($R_{C/T}$) defined by said concentration of said CBD to the concentration of THC,
wherein said first weight ratio ($R_{C/T}$) is at least 5:1;
wherein the topical formulation has a second weight ratio ($R_{A/C}$) defined by said total concentration of said at least one TRPM8 agonist to said concentration of said CBD, wherein said second weight ratio ($R_{A/C}$) is at least 10:1;
and wherein the concentration of lipophilic materials within the topical formulation is at least 90% by weight.

2. The topical formulation of claim 1, wherein said second weight ratio ($R_{A/C}$) is at least 12:1.

3. The topical formulation of claim 1, wherein said second weight ratio ($R_{A/C}$) is within the range of 10:1 to 100:1.

4. The topical formulation of claim 1, wherein said second weight ratio ($R_{A/C}$) is at least 14:1.

5. The topical formulation of claim 1, wherein said second weight ratio ($R_{A/C}$) is at least 17:1.

6. The topical formulation of claim 1, wherein said second weight ratio ($R_{A/C}$) is within the range of 15:1 to 100:1.

7. The topical formulation of claim 1, wherein the concentration of lipophilic materials within the topical formulation is at least 97%.

8. The topical formulation of claim 1, wherein said at least one TRPM8 agonist is said menthol.

9. The topical formulation of claim 1, wherein the concentration of said menthol within the topical formulation is within the range of 6% to 20% by weight.

10. The topical formulation of claim 1, wherein the concentration of said menthol within the topical formulation is within the range of 12% to 20% by weight.

11. The topical formulation of claim 7, wherein the concentration of said menthol within the topical formulation is within the range of 6% to 20% by weight.

12. The topical formulation of claim 1, wherein the total concentration of at least one biocompatible oil within the topical formulation is at least 60% by weight.

13. A topical formulation for application to the skin, the topical formulation comprising:
    (a) cannabidiol (CBD), at a concentration of at least 0.10% by weight;
    (b) at least one agonist of a transient receptor potential melastatin cation channel member 8 (TRPM8), wherein the total concentration of said at least one TRPM8 agonist on an icilin-normalized scale is at least 2.5% by weight;
    (c) optionally, (−)-trans-$\Delta^9$-tetrahydrocannabinol (THC);
    (d) a carrier for said CBD, said at least one TRPM8 agonist, and, if present,
wherein, when said THC is present, the topical formulation has a first weight ratio ($R_{C/T}$) defined by said concentration of said CBD to the concentration of THC,
wherein said first weight ratio ($R_{C/T}$) is at least 5:1;
wherein the topical formulation has a second weight ratio ($R_{A/C}$) defined by said total concentration of said at least one TRPM8 agonist, to said concentration of said CBD,
and wherein said second weight ratio ($R_{A/C}$) is within the range of 10:1 to 100:1;
and wherein the concentration of lipophilic materials within the topical formulation is at least 90% by weight.

14. The topical formulation of claim 13, wherein the concentration of lipophilic materials within the topical formulation is at least 95% by weight.

15. The topical formulation of claim 13, further comprising wax, wherein the concentration of said wax within the topical formulation is within the range of 5 to 35% by weight.

16. The topical formulation of claim 13, wherein the concentration of menthol within the topical formulation is within the range of 6% to 20% by weight.

17. The topical formulation of claim 16, wherein the total concentration of at least one biocompatible oil within the topical formulation is at least 60% by weight.

18. The topical formulation of claim 16, wherein said second weight ratio ($R_{A/C}$) is at least 12:1.

19. The topical formulation of claim 13, wherein said concentration of said CBD is at least 0.20% by weight.

20. The topical formulation of claim 16, wherein said concentration of said CBD is at least 0.45% by weight.

* * * * *